US006647765B2

United States Patent
Downing (10) Patent No.: US 6,647,765 B2
(45) Date of Patent: Nov. 18, 2003

(54) APPARATUS AND METHOD FOR A CLEANING DETECTION DEVICE

(76) Inventor: Eric Downing, 30921 Orwell Rd., Ontario, WI (US) 54651

(*) Notice: Subject to any disclaimer, the term of this patent is extended or adjusted under 35 U.S.C. 154(b) by 220 days.

(21) Appl. No.: 09/943,022

(22) Filed: Aug. 30, 2001

(65) Prior Publication Data

US 2003/0041655 A1 Mar. 6, 2003

(51) Int. Cl.[7] ............................................... G01N 13/02
(52) U.S. Cl. ........................................ 73/104; 116/200
(58) Field of Search .............................. 73/865.8, 104; 116/200, 201, 205, 206, 212

(56) References Cited

U.S. PATENT DOCUMENTS 5,323,729 A * 6/1994 Rubey ......................... 116/201
5,756,885 A * 5/1998 Poku et al. .................... 73/104

* cited by examiner

Primary Examiner—Robert R. Raevis
(74) Attorney, Agent, or Firm—Michael I. Kroll (57) ABSTRACT

The present invention 10 discloses a cleaning device having a base portion 14 with a peel and stick adhesive 20 underside and a clear permeable topside 22 having a color reactive substance 24 contained therein wherein the base portion 14 further includes a malleable flap 12 disposed thereon. The present invention is to be placed in areas to be cleaned such as floors, walls, counters and the like for the purpose of monitoring the efficiency of the people that will be doing the cleaning. The peel and stick adhesive base 20 will maintain the cleaning detector 10 in place and the user will put the malleable flap 12 into a substantially perpendicular position relative to the base portion 14. The malleable flap 12 will be deformed away from the substantially perpendicular position if the area proximal to the present invention 10 has been properly swept, mopped, dusted, etc. Furthermore, the reactive material 24 beneath the permeable top sheet 22 will change color when a substantial amount of moisture has been introduced therein providing the user with useful information regarding areas to be wet mopped and/or wiped down with a liquid.

12 Claims, 8 Drawing Sheets

APPARATUS AND METHOD FOR A CLEANING DETECTION DEVICE

BACKGROUND OF THE INVENTION

1. Field of the Invention

The present invention relates generally to cleaning detectors and more specifically to a cleaning detection device having a base portion with a peel and stick adhesive underside and a clear permeable topside having a color reactive substance contained therein, the base portion further includes a malleable flap thereon. The present invention is to be placed in areas to be cleaned such as floors, walls, counters and the like for the purpose of monitoring the efficiency of the people that will be doing the cleaning. The peel and stick adhesive base will maintain the cleaning detector in place and the user will put the malleable flap into a substantially perpendicular position relative to the base portion. The malleable flap will be deformed if the area proximal to the present invention has been properly swept, mopped, dusted etc. The person monitoring the cleaners with the present invention will know that an area has been neglected if the malleable flap remains substantially perpendicular to the base portion after the cleaning has been completed. Furthermore, the reactive material beneath the permeable top sheet will change color when a substantial amount of moisture has been introduced therein providing the user with useful information regarding areas to be wet mopped and or wiped down with a liquid.

The present invention could be used wherever cleanliness and infection control issues are significant factors. Housekeeping supervisors could monitor cleaners without actually being there at the time and homeowners and businesses could monitor the quality of the services for which they are paying. The cleaning detection device will let people know if the corners are being cleaned, if wall surfaces are getting their scheduled wash-downs, if furniture and appliances and other such items are being moved to be cleaned underneath, if sufficient amounts of cleaning solution are being used or that the mop was too dry to be effective and other quality control questions that previously could only be answered through physical supervision. The present invention could also be used as a training device for new employees.

2. Description of the Prior Art

There are numerous devices that indicate the effectiveness of an item to be cleaned. There are numerous television bracket devices, while these devices may be suitable for the purposes for which they were designed, they would not be as suitable for the purposes of the present invention as hereinafter described.

SUMMARY OF THE PRESENT INVENTION

The present invention discloses a cleaning device having a base portion with a peel and stick adhesive underside and a clear permeable topside having a color reactive substance contained therein wherein the base portion further includes a malleable flap disposed thereon. The present invention is to be placed in areas to be cleaned such as floors, walls, counters and the like for the purpose of monitoring the efficiency of the people that will be doing the cleaning. The peel and stick adhesive base will maintain the cleaning detector in place and the user will put the malleable flap into a substantially perpendicular position relative to the base portion. The malleable flap will be deformed from the substantially perpendicular position if the area proximal to the present invention has been properly swept, mopped, dusted, etc. Furthermore, the reactive material beneath the permeable top sheet will change color when a substantial amount of moisture has been introduced therein providing the user with useful information regarding areas to be wet mopped and/or wiped down with a liquid. The present invention will allow someone to monitor the quality of house or office cleaning being done without actually being there. The present invention will allow a user to see if an area has been swept, mopped, dusted etc., and will also determine if an adequate amount of water or cleaning solution was used when applicable.

A primary object of the present invention is to provide a cleaning detection device having a base portion with a peel and stick adhesive underside for maintaining the present invention in the place that the user selects such as floors, walls, countertops and the like.

Another object of the present invention is to provide a cleaning detection device having a base portion with a permeable sheet on its topside and a color reactive substance therebetween that will change color when a substantial amount of moisture has been introduced therein to notify the user that the area was cleaned with an adequate amount of water or solution.

Yet another object of the present invention is to provide a cleaning detection device wherein the color reactive substance is litmus paper.

Still yet another object of the present invention is to provide a cleaning detection device wherein the color reactive substance responds to specific solutions to inform the user whether the proper cleaning agent is being used or if the cleaners are just using water and not the required cleaning agent.

Another object of the present invention is to provide a cleaning detection device wherein the base portion has a malleable flap that is placed into a substantially perpendicular position relative to the base portion once the device is situated in place. The flap will be deformed into a non-perpendicular position when contact is made with a broom, mop, cloth or other such cleaning device to inform the user that the area has been cleaned.

Yet another object of the present invention is to provide a cleaning detection device with a peel and stick base portion that could have either a malleable flap or a permeable sheet covering a color reactive material or a combination thereof.

Still yet another object of the present invention is to provide a cleaning detection device that is simple and easy to use.

Another object of the present invention is to provide a cleaning detection device that is economical in cost to manufacture.

Additional objects of the present invention will appear as the description proceeds.

To the accomplishments of the above and related objects, this invention may be embodied in the form illustrated in the accompanying drawings, attention being called to the fact, however, that the drawings are illustrative only, and that changes may be made in the specific construction illustrated and described in the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views in which.

LIST OF REFERENCE NUMERALS

With regard to reference numerals used, the following numbering is used throughout the drawings.

10 present invention
12 distortable material
14 base
16 reception window
18 doctor's office
20 peel off backing
22 permeable sheet
24 liquid reactive substance
26 holes
28 adhesive

DETAILED DESCRIPTION OF THE PREFERRED EMBODIMENT

The following discussion describes in detail one embodiment of the invention and several variations of that embodiment. This discussion should not be construed, however, as limiting the invention to those particular embodiments since practitioners skilled in the art will recognize numerous other embodiments as well. For a definition of the complete scope of the invention, the reader is directed to the appended claims.

Figure 1:
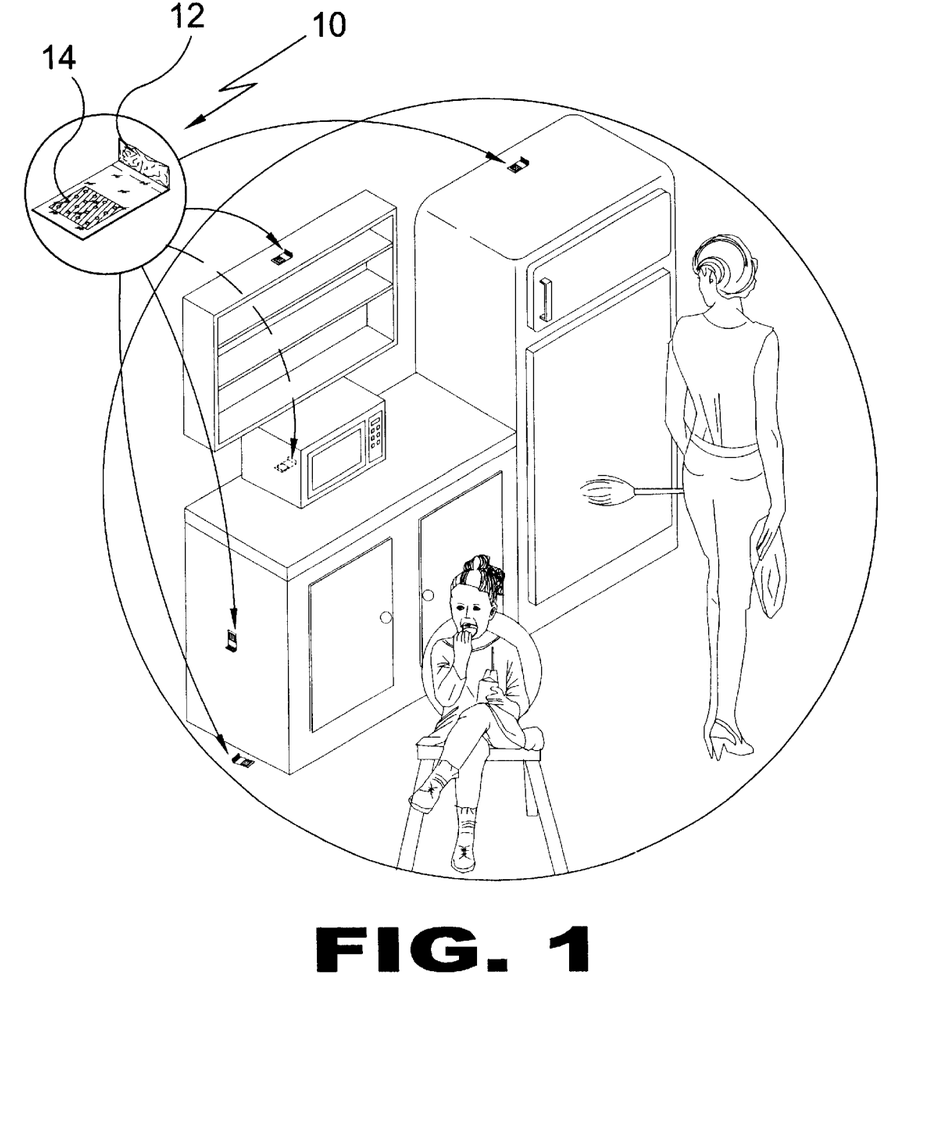
FIG. 1 is a perspective view of the present invention in use.

Turning to FIG. 1, shown therein is a perspective view of the present invention 10 in use. The cleaning detection device of the present invention 10 is a monitor or indicator showing whether or not a particular area has been cleaned. The present invention comprises an easily distortable or malleable material 12 and a base portion 14 having an applied fluid indicator thereon. The easily distortable material 12 indicates whether or not a force has been applied thereto. The distortable material 12 can be any malleable material such as tin foil or the like. The applied liquid indicator 14 can be any substance such as litmus paper that is color-reactive when introduced to fluids.

Figure 2:
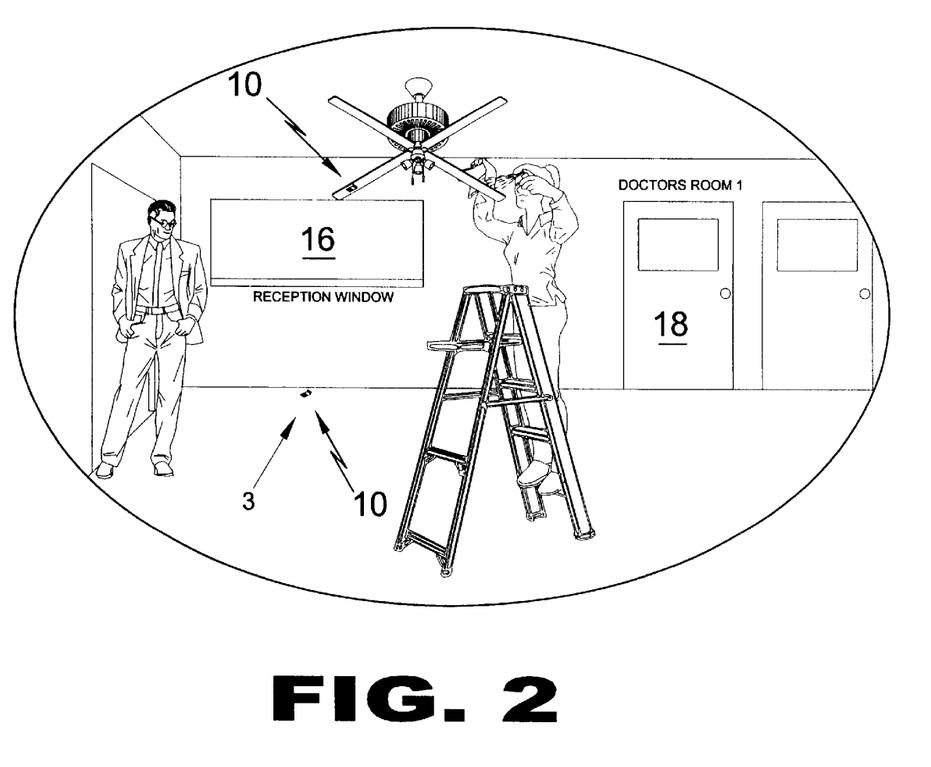
FIG. 2 is an illustrative view of the present invention in use.

Turning to FIG. 2, shown therein is an illustrative view of the present invention 10 in use. The cleaning detection 10 could be used wherever cleanliness and infection control issues are significant factors. Housekeeping supervisors can monitor the cleaners and inspect how thoroughly they have cleaned without actually being there at the time. The present invention could be used in hospitals, doctor's offices, nursing homes, restaurants or anywhere that cleaners are hired. Shown are a reception window 16 and the door 18 to a doctor's office.

Figure 3:
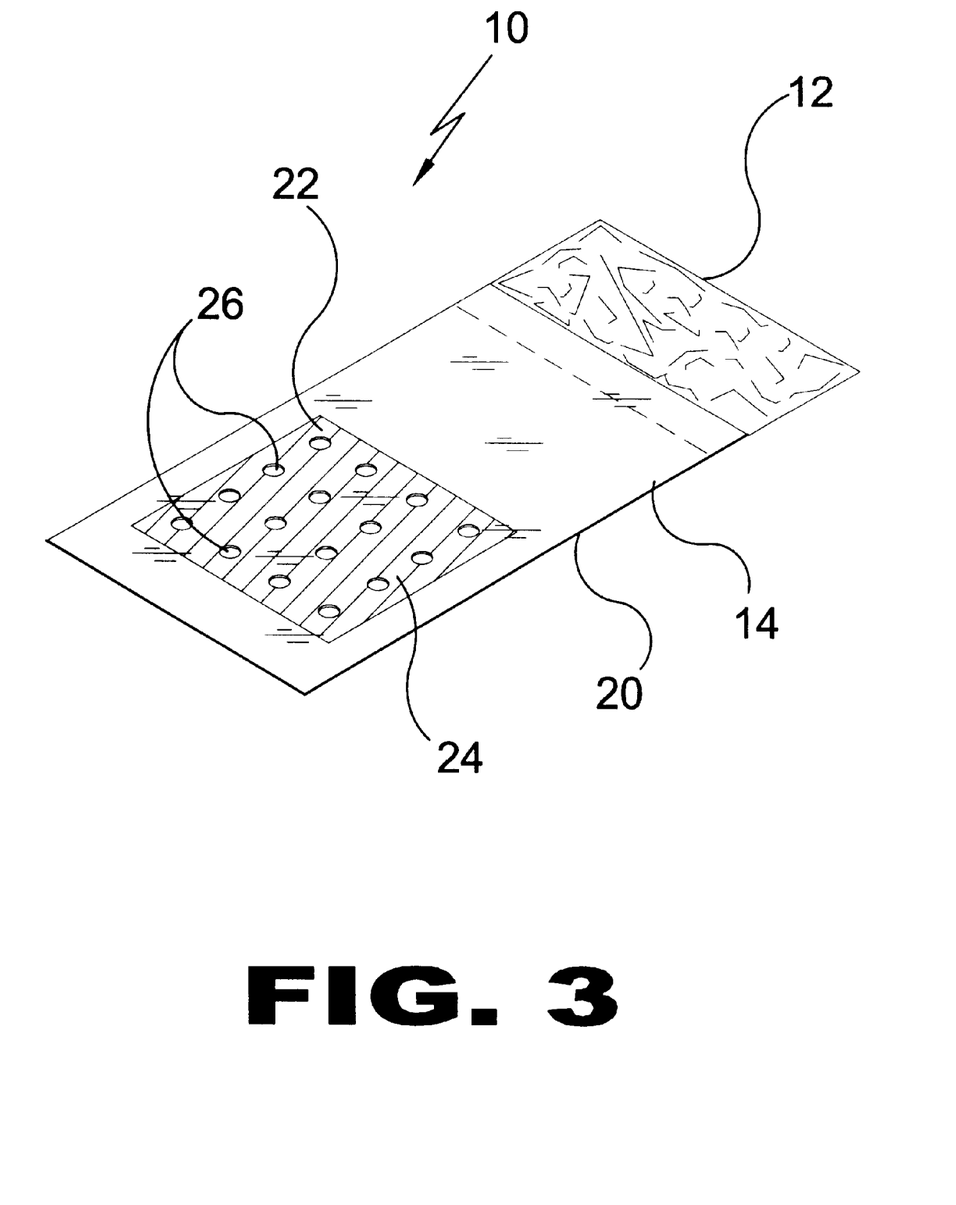
FIG. 3 is a perspective view of the present invention.

Turning to FIG. 3, shown therein is a perspective view of the present invention 10 comprising a generally planar base portion 14 having a peel and stick adhesive underside 20 and a topside covered with a permeable sheet 22 having multiple holes 26 therein having a liquid reactive substance 24 therebetween. One end of the base 14 portion further includes a malleable or distortable sheet or material 12 disposed thereon.

Figure 4:
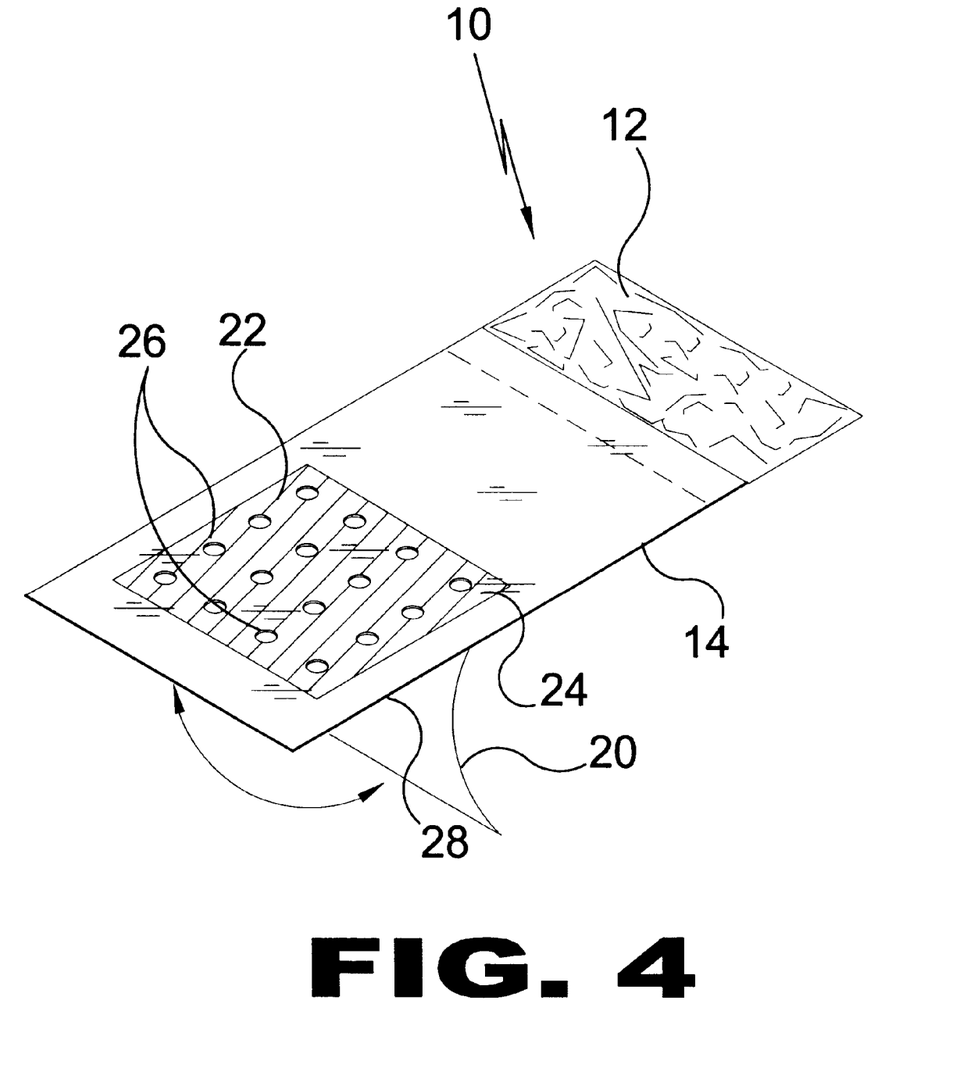
FIG. 4 is a perspective view of the present invention.

Turning to FIG. 4, shown therein is a perspective view of the present invention 10. The base 14 of the cleaning detection device has a peel off backing 20 protecting the adhesive 28 until the device is ready to be used. Once the backing 20 is peeled off the present invention is ready to place into the selected area by sticking it onto the surface to be monitored. Other elements previously disclosed are also shown.

Figure 5:
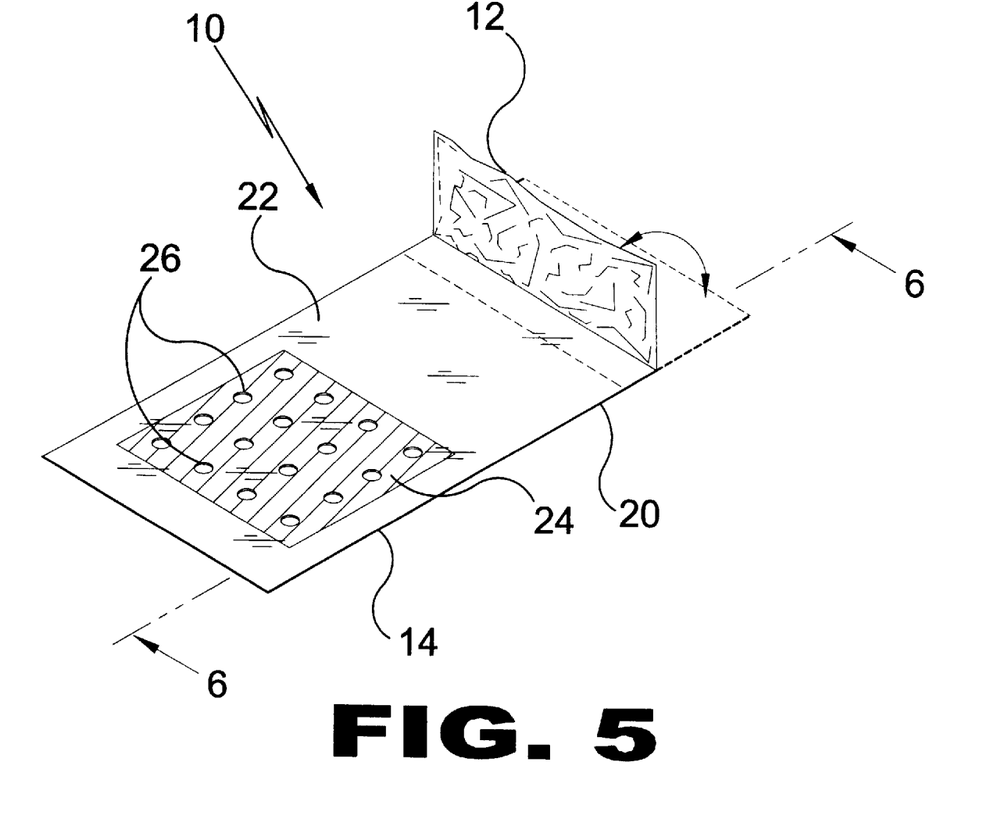
FIG. 5 is a perspective view of the device of the present invention.

Turning to FIG. 5, shown therein is a perspective view of the present invention 10 showing the easily deformable malleable flap 12 being foil or the like folded to a substantially perpendicular position relative to the base portion 14 whereby any applied force will deform the material 12 away from the perpendicular position indicating cleaning has taken place. If the proximal area has not been cleaned the malleable flap 12 will remain in the substantially perpendicular position and the litmus material 24 or the like will retain its original color. The permeable sheet 22 could be clear tape of the like. Other elements previously disclosed are also shown.

Figure 6:
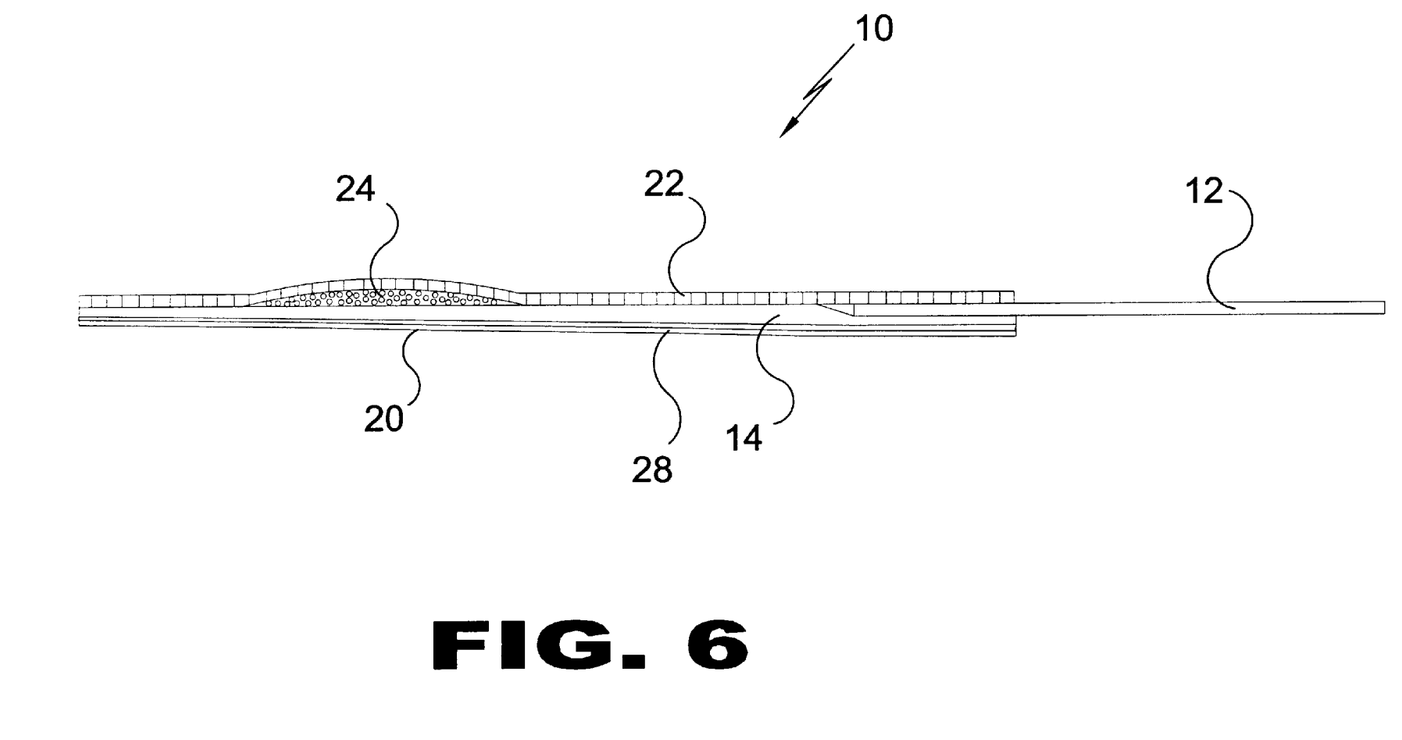
FIG. 6 is a cross-sectional side view of the present invention.

Turning to FIG. 6, shown therein is a cross sectional side view of the present invention 10 having a base portion 14 with a peel and stick paper layer 20 on an adhesive 28 underside, a permeable sheet 22 on the top side with a liquid reactive substance 24 therebetween and a deformable malleable sheet 12 extending therefrom from one end.

Figure 7:
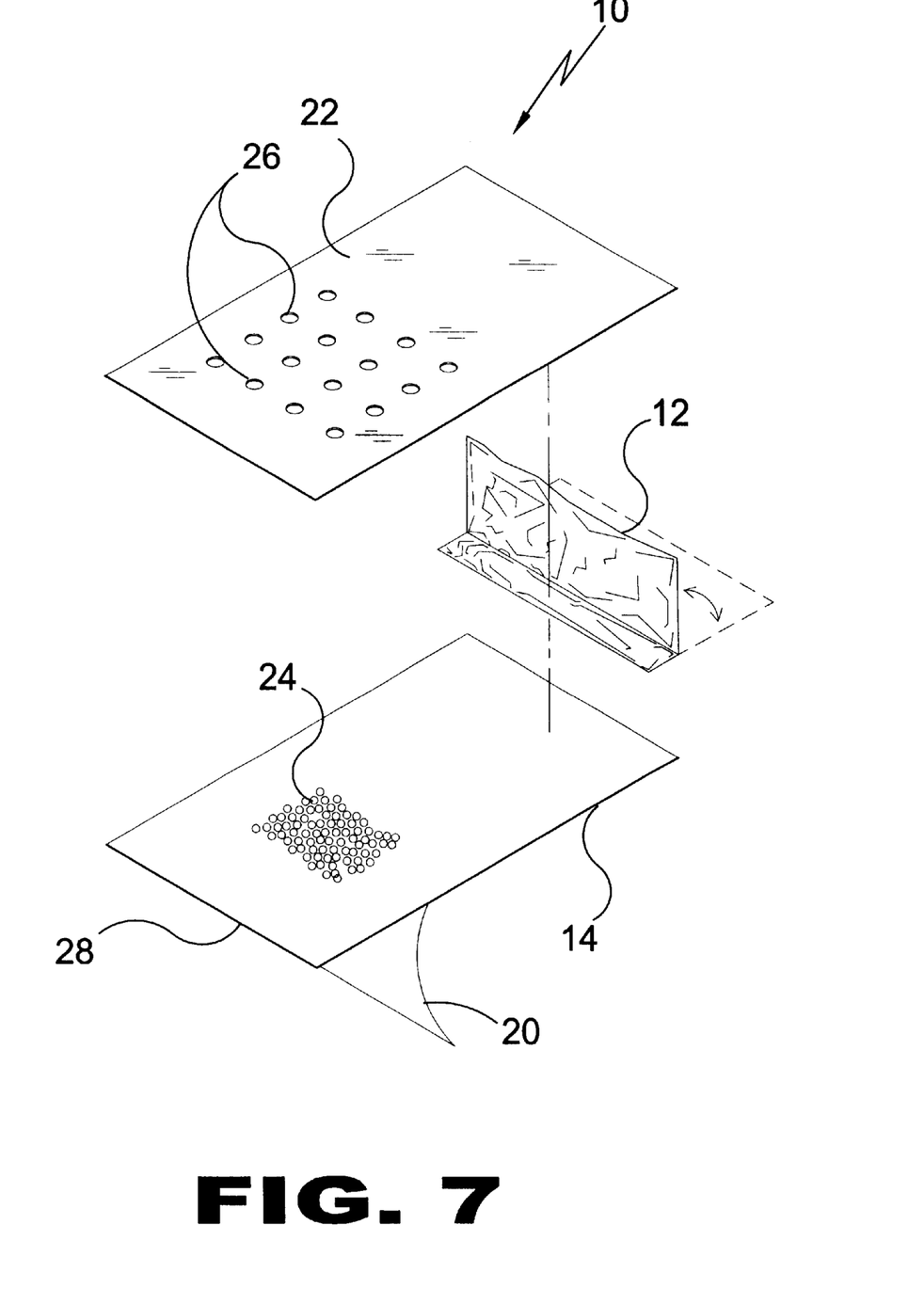
FIG. 7 is an exploded view of the present invention.

Turning to FIG. 7, shown therein is an exploded view of the present invention 10 showing the various layers and components as previously disclosed. The reactive substance 24 can be litmus paper, colored powder or any other water reactive color changing material. The malleable sheet 22 can be made of any material that will deform under any minimal contact such as dusting.

Figure 8:
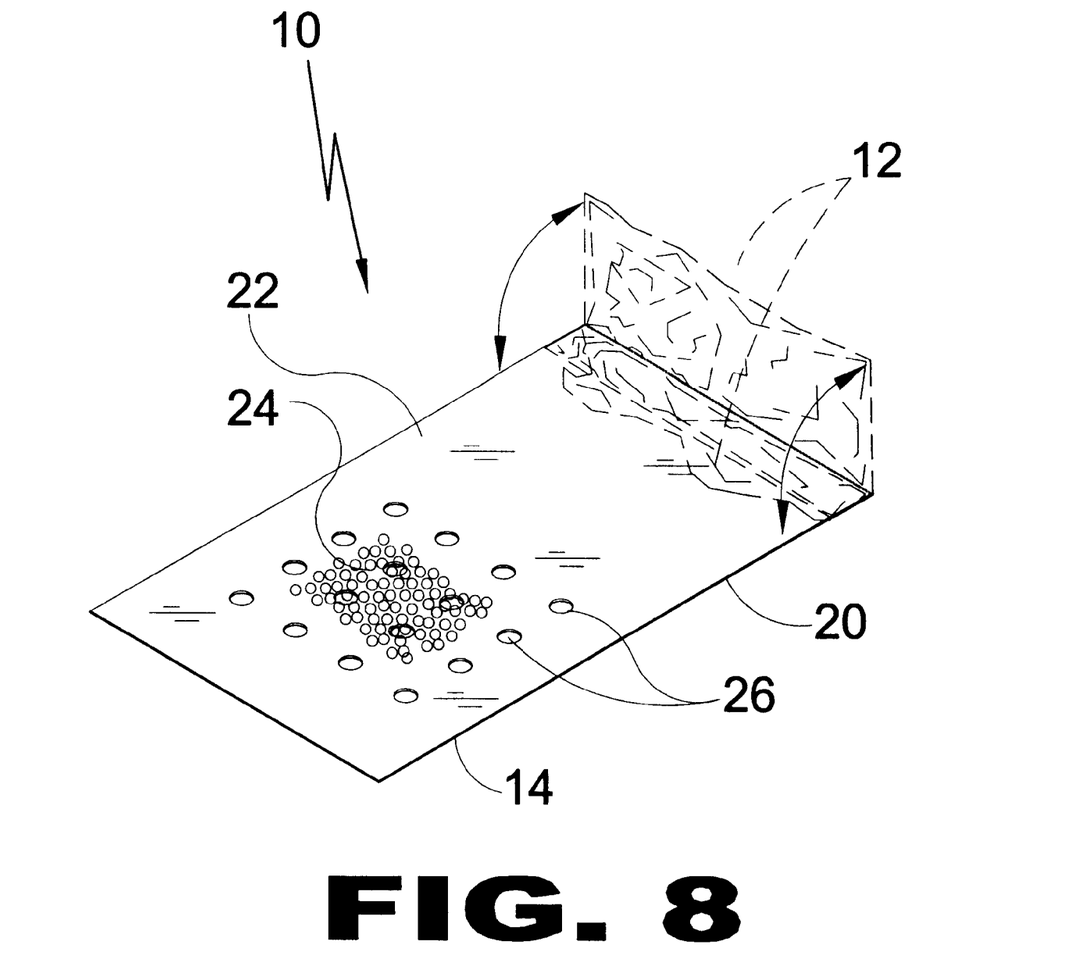
FIG. 8 is a detailed view of the present invention in use.

Turning to FIG. 8, shown therein is a perspective view of the present invention 10 employed. The malleable sheet 12 is turned into a substantially perpendicular position relative to the base portion 14. When cleaning is performed the malleable material 12 will become flattened or deformed. If the area where the cleaning detection device 10 is placed has not been cleaned the malleable flap 12 will remain in the substantially perpendicular position and the litmus material 24 will retain its original color as an indication that cleaning was not performed. Other elements previously disclosed are also shown.

What is claimed to be new and desired to be protected by Letters Patent is set forth in the appended claims.

I claim:

1. An apparatus for monitoring a surface in order to determine if the surface has been cleaned, comprising:

a) a generally planar base member, said base member being generally rectangular shaped, said base member having a top side and a bottom side;

b) an adhesive disposed on said bottom side of said base member for attaching said base member to the surface to be cleaned;

c) a peel-off layer disposed on said adhesive layer in order to protect said adhesive layer;

d) a permeable sheet disposed on said top side of said base member, said permeable sheet having a plurality of holes therein so that moisture can pass therethrough;

e) a moisture reactive substance disposed between said permeable sheet and said base member to indicate the presence of moisture; and, f) a malleable sheet disposed on one end of said base member to indicate if the surface has been cleaned.

2. The apparatus of claim 1, wherein said permeable sheet is tape.

3. The apparatus of claim 2, wherein said permeable sheet is clear tape.

4. The apparatus of claim 3, wherein said moisture reactive substance further comprises litmus paper.

5. The apparatus of claim 4, wherein said moisture reactive substance further comprises powder.

6. The apparatus of claim 5, wherein said moisture reactive substance further comprises colored powder.

7. The apparatus of claim 6, wherein said malleable sheet further comprises tin foil.

8. The apparatus of claim 7, wherein said moisture reactive substance is disposed near a first end of said base member.

9. The apparatus of claim 8, wherein said malleable sheet is disposed on a second end of said base member.

10. A method for monitoring a surface in order to determine if the surface has been cleaned, comprising the steps of:

a) providing a generally planar base member, the base member being generally rectangular shaped, having a top side and a bottom side;

b) placing an adhesive on the bottom side of the base member for attaching the base member to the surface to be cleaned;

c) attaching a peel-off layer to the adhesive layer in order to protect the adhesive layer;

d) providing a permeable sheet on the top side of the base member, the permeable sheet having a plurality of holes therein so that moisture can pass therethrough;

e) placing a moisture reactive substance between the permeable sheet and the base member near one end of the base member to indicate the presence of moisture; and, f) attaching a malleable sheet on a second end of the base member to indicate if the surface has been cleaned.

11. The method of claim 10, further comprising the step of moving the malleable sheet into an upright position substantially perpendicular to the base member to determine if the surface has been cleaned.

12. The method of claim 11, further comprising the step of removing the peel-off layer from the adhesive in order to attach the base member to the surface to be monitored.

* * * * *